United States Patent [19]

Hendler et al.

[11] Patent Number: 5,114,957

[45] Date of Patent: May 19, 1992

[54] TOCOPHEROL-BASED ANTIVIRAL AGENTS AND METHOD OF USING SAME

[75] Inventors: Sheldon S. Hendler, La Jolla; Robert Sanchez, Carlsbad, both of Calif.

[73] Assignees: Biodor U.S. Holding; Vyrex Corporation, both of La Jolla, Calif.

[21] Appl. No.: 520,633

[22] Filed: May 8, 1990

[51] Int. Cl.⁵ .................... A61K 31/44; A61K 31/355
[52] U.S. Cl. ..................................... 514/356; 514/458
[58] Field of Search ................................. 514/458, 356

[56] References Cited

PUBLICATIONS

Chem. Abst. 111, 167396f (1989).
Machlin, L. J., ed., *Handbook of Vitamins*, Chapter 3, "Vitamin E", Marcel Dekker, Inc., 1983.
Mukai, et al., *J. Org. Chem.* 54: 557–560 (1989).
Reimund, E., *Medical Hypotheses* 23: 39 (1987).
*The Merck Index*, 10th ed., Merck & Co., Inc., 1983, p. 1437.

*Primary Examiner*—S. J. Friedman

[57] ABSTRACT

This invention relates to methods for inhibiting viral and retroviral replication and for treating viral and retroviral infections via the administration of compositions containing Vitamin E, tocopherol, or a tocopherol derivative and, more particularly, compositions containing α-tocopherol or a pharmaceutically effective prodrug thereof.

28 Claims, No Drawings

TOCOPHEROL-BASED ANTIVIRAL AGENTS AND METHOD OF USING SAME

BACKGROUND OF THE INVENTION

Vitamin E, which is known by many alternative appellations (including tocopherol), is required by all animals, including those as diverse in physiology and environment as humans and fish, for example. As used in many applications, and as used herein, the terms "Vitamin E" or "tocopherol" are used to mean any mixture of physiologically active tocopherols, including Vitamin E acetates and other prodrugs of Vitamin E, as well as tocopherol derivatives, which include Vitamin $K_1$-chromanol and Vitamin $K_1$-chromenol. Natural α-tocopherol, one of the more common tocopherols, is usually found with beta-, gamma- and delta-tocopherols. (See, e.g., *The Merck Index*, 10th ed., Merck & Co., Inc., 1983, at page 1437.)

In general, dietary requirements range from about 3 to about 70 IU (international units) per kilogram of dietary intake in animals. (See, e.g., Machlin, L.J., ed., *Handbook of Vitamins*, Marcel Dekker, Inc., 1983, particularly Chapter 3, "Vitamin E".) Vitamin E is widely distributed in nature, with the more common dietary sources being meats, dairy products, eggs, and vegetable oils.

Natural Vitamin E encompasses a family of compounds and isomers, all of which are phenolic isoprenoid derivatives. Of these compounds, D-α-tocopherol is the most abundant and has the highest biological activity. Many commercial products are synthetically produced and are based on the racemic mixture DL-α-tocopherol. DL-α-tocopherol acetate is a common commercial form, and its biological activity is expressed as 1.00 IU per milligram (mg). The biological activity of tocopherol ester is almost equivalent to that of tocopherol, to which it is rapidly hydrolyzed after ingestion. Other examples of prodrug derivatives are tocopheryl succinate, tocopheryl nicotinate and tocopheryl phosphate.

Vitamin E shows an abundant variety of beneficial biological activities which have been explored and studied since about 1925, and many new applications remain to be described. We have now discovered and shown for the first time that Vitamin E has substantial antiviral activity. In particular, we have found that the antiviral activity of Vitamin E is demonstrated by its protective effect against HIV-1 infection, as illustrated in a model using Molt-3 cells.

It is well known that diseases associated with viral and retroviral infections are major medical, veterinary and agricultural problems in the United States and worldwide. Diseases of known viral origin include chicken pox, the common cold, cytomegalovirus disease (CMV), dengue fever, encephalitis, hoof-and-mouth disease, herpes infections, influenza, keratoconjunctivitis, measles, mumps, Newcastle disease, poliomyelitis, rabies, rubella, scrapie, shingles, smallpox, tick fever, West Nile Fever, and yellow fever, to name but a few. An especially serious problem at the present time is the rapid escalation in reported cases of AIDS (Acquired Immune Deficiency Syndrome), whose causative agent is strongly suspected to be HIV (Human Immunodeficiency Virus).

There are urgent and compelling reasons for the development of more efficacious and safer treatments of viral and retroviral infections. It is estimated that at least one and a half million people in the United States alone have been infected with the human immunodeficiency (HIV) or AIDS virus. HIV causes a decay of a major arm of the immune system, the immune helper cells (T4 helper or CD4+ helper cells). This decay leads to a wide spectrum of diseases, generally called HIV disease, of which AIDS is the most serious and devastating form. It is anticipated that over one third of the budget for medical care in the U.S. will be consumed on HIV disease. There is an escalating incidence of other viral diseases as well. For example, cytomegalovirus (CMV) infection is rapidly increasing in the teenage population of the United States.

Therefore, in response to this pervasive need for safer and more efficacious treatments of viral and retroviral infections, we now describe our findings and propose compositions and methods for treatment of viral and retroviral infections using Vitamin E-based compositions.

SUMMARY OF THE INVENTION

This invention relates to methods for using compositions containing Vitamin E, tocopherol, or tocopherol derivatives for inhibiting viral and retroviral infections. The invention is also directed to methods for using the disclosed pharmaceutical compositions to inhibit viral and retroviral replication and infections in vivo.

Therefore, according to one aspect of the invention, a method for treating viral infections in a living organism comprising administering to a living organism an effective antiviral amount of a composition containing Vitamin E is disclosed. In another embodiment, the method comprises administration of a tocopherol- or tocopherol derivative-containing composition. In another aspect, the method comprises the administration of a DL-α-tocopherol-containing composition. In additional variations, the method comprises the administration of compositions containing α-tocopherol, DL-α-tocopherol, D-α-tocopherol, Vitamin $K_1$-chromanol, Vitamin $K_1$-chromenol, tocotrienols, or pharmaceutically effective prodrugs thereof. Examples of prodrugs include DL-α-tocopherol acetate, tocopheryl succinate, tocopheryl nicotinate, or tocopheryl phosphate.

In a preferred application, the organism is an animal. More preferably, the animal is a mammal, and even more preferably, a human.

Yet another aspect suggests a method for inhibiting viral replication in a living organism comprising administering to a living organism an effective antiviral amount of a composition containing Vitamin E is disclosed. In another embodiment, the composition contains an effective antiviral amount of a tocopherol or a tocopherol derivative. In another aspect, the method comprises the administration of a tocopherol-containing composition. In additional variations, the method comprises the administration of compositions containing α-tocopherol, DL-α-tocopherol, D-α-tocopherol, Vitamin $K_1$-chromanol, Vitamin $K_1$-chromenol, tocotrienols, or pharmaceutically effective prodrugs thereof. Examples of such prodrugs include DL-α-tocopherol acetate, tocopheryl succinate, tocopheryl nicotinate, or tocopheryl phosphate. In a preferred application, the organism is an animal. More preferably, the animal is a mammal, and even more preferably, a human.

A further embodiment suggests that the disclosed compositions may be administered via various means, including parenteral, oral, intraperitoneal, topical or transdermal administration. In another aspect, the compositions may be administered via inhalation, or liposomally.

DETAILED DESCRIPTION

The above-referenced tocopherol- or Vitamin E-containing compositions can be administered topically, orally or parenterally by subcutaneous, intramuscular, intravenous or intraperitoneal injection or by implantation or the like, oral administration being preferred. DL-α-tocopherol, D-α-tocopherol, α-tocopherol, tocotrienols, or pharmaceutically effective prodrugs thereof are preferably administered as pharmaceutical compositions in dosage unit form. Such compositions can be prepared by known techniques, for example, tableting or encapsulation. For administration to humans, the dosage units of the compositions, including the pharmaceutically effective prodrugs, preferably contain from about 100 milligrams (mg) to about one gram of the active ingredient. Dosage units, adapted for oral administration, such as tablets, capsules, lozenges, and the like, may contain up to about 2 grams of active ingredient, albeit they preferably contain from about 200 mg to about 500 mg of the active ingredient, for ease of administration. Dosages may also be administered in liquid forms. The compositions can also be administered as formulations adapted to be fed as part or all of the animal's diet. The compositions of the present invention may be administered in various efficacious amounts. The preferred dosage range of active ingredient for adult humans is from about 0.2 grams (gm) to about 5 gm per day, with a range of 1 gm to 3 gm per day being somewhat more preferable.

The invention can be better understood by way of the following examples which are representative of the preferred embodiments thereof, but which are not to be construed as limiting the scope of the invention.

EXAMPLE I

In Vitro Inhibition Tests

We have observed that Vitamin E exerts a protective effect against viral infections and the resulting pathologies. The model used herein is the infection of Molt-3 cells by HIV-1 (human immunodeficiency virus type 1), the putative causative agent of AIDS disease (Acquired Immune Deficiency Syndrome). Molt-3 cells are a clonal derivative of a lymphocyte (T-cell) line of Japanese origin, which may be obtained from the National Institutes of Health, Bethesda, MD. The progression of infection in this model is accompanied by increases in syncytial cell formation and increases in levels of p24, a component protein of the viral core. Both of these parameters can be measured experimentally.

D-α-tocopherol (Longs Drugs, Walnut Creek, Calif.) was dissolved in DMSO to a concentration of 3% w/v and was used as a stock solution for delivery of the desired quantity. All solutions were adjusted to contain a final concentration of 1% DMSO. Both the Molt-3 cells (which are an HTLV-1 transformed cell line particularly sensitive to infection by HIV-1) and the HIV-1 were exposed to DL-α-tocopherol for 4 hours and 1 hour, respectively, at the indicated concentration before mixing, and then the incubation was carried out at 37° C.

Testing Protocol

Fifteen ml of each of the media was prepared at the indicated concentrations of compound and/or solvent. A washed pellet consisting of $1.5 \times 10^6$ cells of Molt-3 (a clonal derivative of a lymphocyte (T-cell) line of Japanese origin, obtained from the National Institutes of Health, Bethesda, Md.) was suspended in 1 ml of each compound or control medium. Each tube was incubated with occasional shaking at 37° for four hours.

During the last hour of the preincubation period, Molt-3 grown HIV-1 was diluted into 1 ml each of the media to provide 200 $TCID_{50}$ units. Polybrene (10 μg/ml) was included in each tube.

The cells were pelleted and resuspended in the virus-containing media, then incubated for 60 minutes at 37° with occasional shaking. The cells were then pelleted and resuspended in 5 ml of each medium. Each cell pellet was washed twice in complete growth medium, then transferred to labeled 6-well trays.

On a daily basis, giant cells and syncytia were counted. At the same time, 0.5 ml of the culture was and frozen at −70° C. Fresh medium was used for replenishment.

At the end of three days, p24 was measured by antigen capture immunoassay. A p24 immunodiagnostic test kit (Coulter Corporation, Hialeah, Fla.) was used for this purpose. At the end of a 4–5 day period, uninfected cells were tested for viability by Trypan Blue exclusion.

Results

Syncytium cells were counted by microscopy, and p24 levels were measured by antigen capture immunoassay. The averaged results over days 5, 6 and 7 were as follows:

| Concentration of D-α-tocopherol μg/mL | % Reduction of syncytium formation (a) | % Reduction of HIV p24 (b) |
| --- | --- | --- |
| 30 | 94 | 75 |
| 10 | 86 | 51 |
| 3 | 51 | 34 |
| 1 | 25 | 32 |

(a) relative to syncytium formation in the absence of D-α-tocopherol, and corrected for syncytium formation in the absence of virus.
(b) relative to p24 formation in the absence of D-α-tocopherol.

We used BHT (2,6-di-tert-butyl-4-methylphenol) as a "positive control", i.e., comparing results obtained when using BHT against those obtained with Vitamin E, as BHT is similar to Vitamin E in certain aspects, as noted below. BHT is a lipophilic hindered phenol with antioxidant properties, and it is suspected to have an effect against a variety of viruses (see, e.g., Reimund, *Medical Hypotheses*, 23, 39 (1987)). The BHT used herein was obtained from Aldrich Chem. Co. (Milwaukee, Wis., Cat. No. D4,740-4). Solutions were prepared in exactly the same way as for D-α-tocopherol. BHT as a "positive control" gave the following results:

| Concentration of BHT μg/mL | % Reduction of syncytium formation | % Reduction of HIV p24 |
| --- | --- | --- |
| 30 | toxic | toxic |
| 10 | 79 | 93 |
| 3 | 76 | 82 |

-continued

| Concentration of BHT μg/mL | % Reduction of syncytium formation | % Reduction of HIV p24 |
|---|---|---|
| 1 | 69 | 34 |

The fact that Vitamin E produced significant reduction in both syncytium formation and in HIV p24 confirmed our belief that Vitamin E had great potential for use as a potent, and generally non-toxic, antiviral agent. Our suspicion in that regard was strengthened even more when the results observed with the use of Vitamin E compared well with those we obtained using BHT, which we have already shown to be a potent inhibitor of viral and retroviral infections.

EXAMPLE II

Administration Protocols

A. Topical

For topical applications, Vitamin E in its various forms may be applied directly or in combination with pharmaceutically acceptable excipients such as creams, ointments, salves, moisturizers or similar formulations. In one example, DL-α-tocopherol is applied full-strength four times daily to lip "cold sores" (herpes simplex viral infection sites). Discomfort during the infection is noticeably reduced, and severity and duration of the infection is reduced on the order of about 30–50%.

B. Oral

For oral applications, any of the commonly available forms of the vitamin (e.g. DL-α-tocopherol, D-α-tocopherol, natural tocopherol mixtures, and any of the prodrugs of the foregoing, such as the acetates, succinates, nicotinates, or phosphates, to list a few examples) may be taken orally in either a single dose or in divided doses, on a daily basis. The vitamin may be taken in pure form, or in admixture with foods, or with excipients such as vegetable oils. It may also be taken in admixture with other vitamins or food supplements. In a typical example, 1200 units (1.20 gm) of DL-α-tocopherol acetate are taken daily, in the form of soft gelatin capsules containing 200 units each, two capsules taken with each meal.

C. Intravenous/Parenteral

For intravenous (I.V.) and parenteral applications, it is essential that careful medical supervision and monitoring take place. Dosages and dose rates generally should be controlled on an individual basis. Examples of suitable formulations of Vitamin E for injection include water-soluble mixtures (e.g., succinate ester in an aqueous buffer), aqueous dispersions (e.g., acetate ester in a detergent-promoted emulsion), and liposomal dispersions (e.g., acetate ester in a phospholipid-based liposome).

The preparation of such mixtures, including liposomal preparations, uses techniques generally known in the art. For example, liposomes can be prepared from a wide variety of lipids, including phospholipids, glycolipids, steroids, charged amphiphilic compounds, and the like. Illustrative examples of phospholipids include lecithin, sphingomyelin, and the like. Representative examples of steroids include cholesterol, lanosterol, and the like.

Although the invention has been described in the context of particular embodiments, it is intended that the scope of coverage of the patent not be limited to those particular embodiments, but be determined by reference to the following claims.

We claim:

1. A method for treating viral infections in a living organism infected with a virus comprising administering to said living organism an effective antiviral amount of tocopherol or a pharmaceutically effective prodrug thereof.

2. The method of claim 1, wherein said tocopherol is α-tocopherol.

3. The method of claim 1, wherein said tocopherol is DL-α-tocopherol.

4. The method of claim 1, wherein said tocopherol is D-α-tocopherol.

5. The method of claim 1, wherein said prodrug is DL-α-tocopherol acetate.

6. The method of claim 1, wherein said prodrug is tocopheryl succinate.

7. The method of claim 1, wherein said prodrug is tocopheryl nicotinate.

8. The method of claim 1, wherein said prodrug is tocopheryl phosphate.

9. The method of claim 1, wherein said organism is an animal.

10. The method of claim 9, wherein said animal is a mammal.

11. The method of claim 10, wherein said mammal is a human.

12. A method for inhibiting viral replication in a living organism exposed to a virus comprising administering to said living organism an effective antiviral amount of tocopherol or a pharmaceutically effective prodrug thereof.

13. The method of claim 12, wherein said tocopherol is α-tocopherol.

14. The method of claim 12, wherein said tocopherol is DL-α-tocopherol.

15. The method of claim 12, wherein said tocopherol is D-α-tocopherol.

16. The method of claim 12, wherein said prodrug is DL-α-tocopherol acetate.

17. The method of claim 12, wherein said prodrug is tocopheryl succinate.

18. The method of claim 12, wherein said prodrug is tocopheryl nicotinate.

19. The method of claim 12, wherein said prodrug is tocopheryl phosphate.

20. The method of claim 12, wherein said organism is an animal.

21. The method of claim 20, wherein said animal is a mammal.

22. The method of claim 21, wherein said mammal is a human.

23. The method of claim 1 or 12, wherein said compound is administered parenterally.

24. The method of claim 1 or 12, wherein said compound is administered orally.

25. The method of claim 1 or 12, wherein said compound is administered intraperitoneally.

26. The method of claim 1 or 12, wherein said compound is administered topically or transdermally.

27. The method of claim 1 or 12, wherein said compound is administered via inhalation.

28. The method of claim 1 or 12, wherein said compound is administered liposomally.

* * * * *